United States Patent [19]

Phillips

[11] 4,065,093
[45] Dec. 27, 1977

[54] FLOW CONTROL DEVICE

[75] Inventor: Thomas E. Phillips, Ingleside, Ill.

[73] Assignee: Baxter Travenol Laboratories, Inc., Deerfield, Ill.

[21] Appl. No.: 689,321

[22] Filed: May 24, 1976

[51] Int. Cl.² ............................................. F16K 7/06
[52] U.S. Cl. .......................................... 251/6; 251/342
[58] Field of Search ................................. 251/4–10, 251/61.1, 342

[56] References Cited

U.S. PATENT DOCUMENTS

| 1,917,613 | 7/1933 | Szumkowski | 251/8 X |
| 3,039,733 | 6/1962 | Mattioli | 251/5 |
| 3,099,429 | 7/1963 | Broman | 251/6 |
| 3,685,787 | 8/1972 | Adelberg | 251/6 |
| 3,779,507 | 12/1973 | Clarke | 251/4 X |

FOREIGN PATENT DOCUMENTS 1,011,887  4/1952  France .......................... 251/4

Primary Examiner—Martin P. Schwadron
Assistant Examiner—Richard Gerard
Attorney, Agent, or Firm—Eugene M. Cummings; Paul C. Flattery; John P. Kirby, Jr.

[57] ABSTRACT

A flow control device for a fluid flow system includes a conduit having a cylindrical insert member disposed within. The insert member includes an axially-extending depression, and a flow bypass channel of progressively increasing cross-section within the depression. A roller mounted for movement along the wall compresses the wall into the depression to restrict flow to the underlying portion of the bypass channel. By positioning the roller the operative area of the bypass channel is varied to obtain a desired flow rate.

12 Claims, 8 Drawing Figures

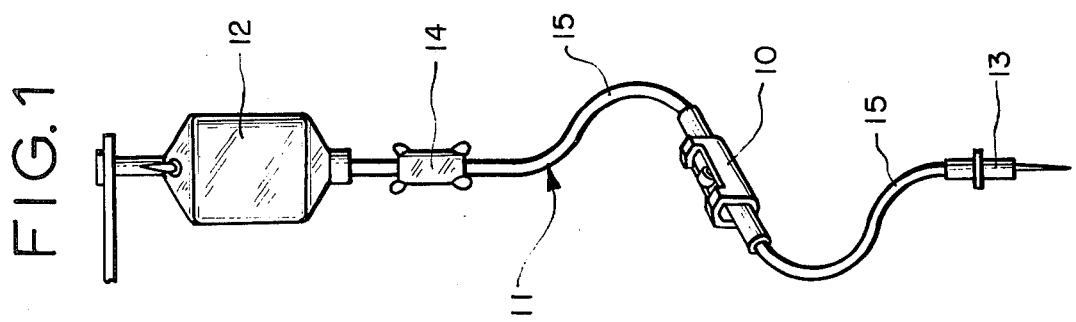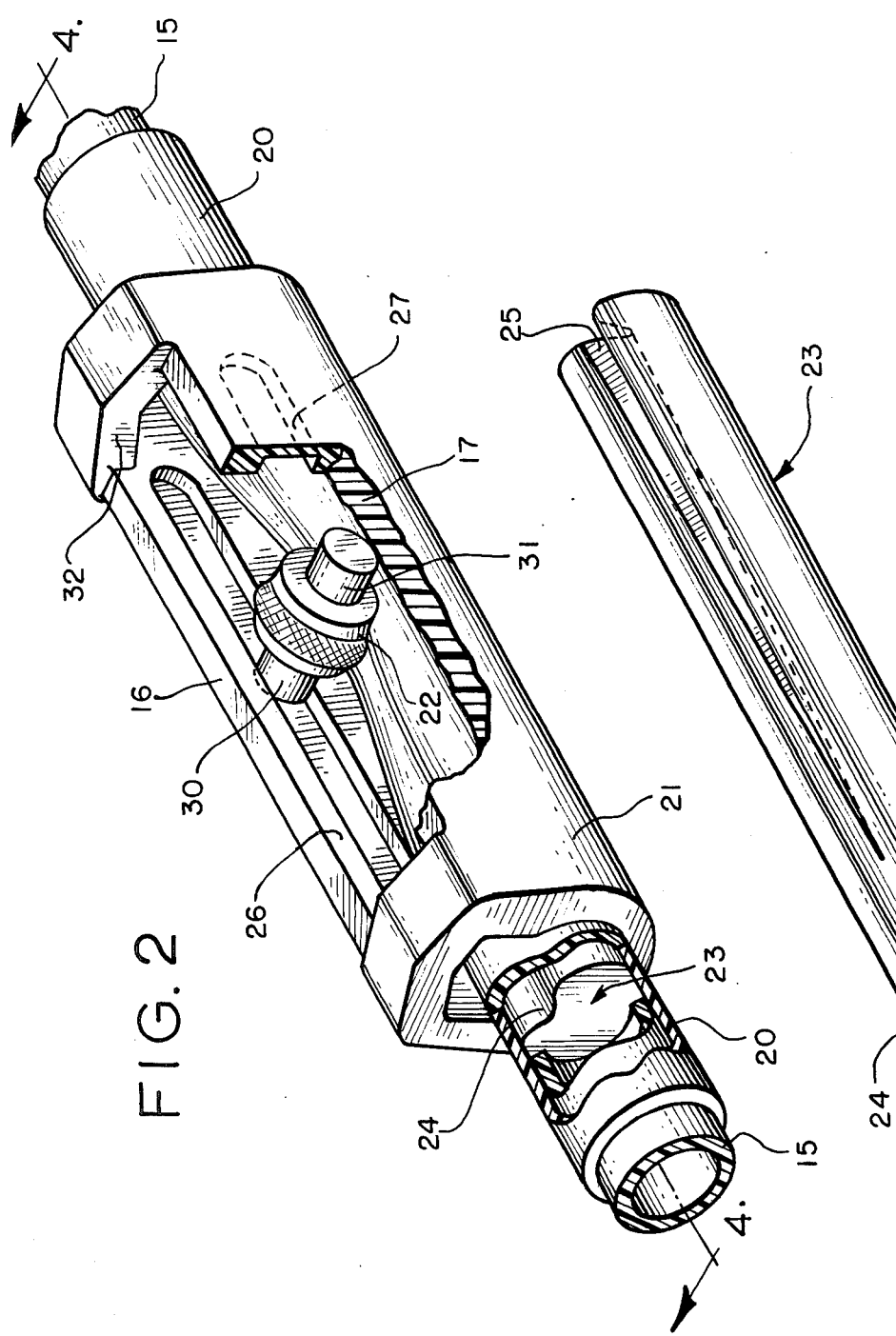

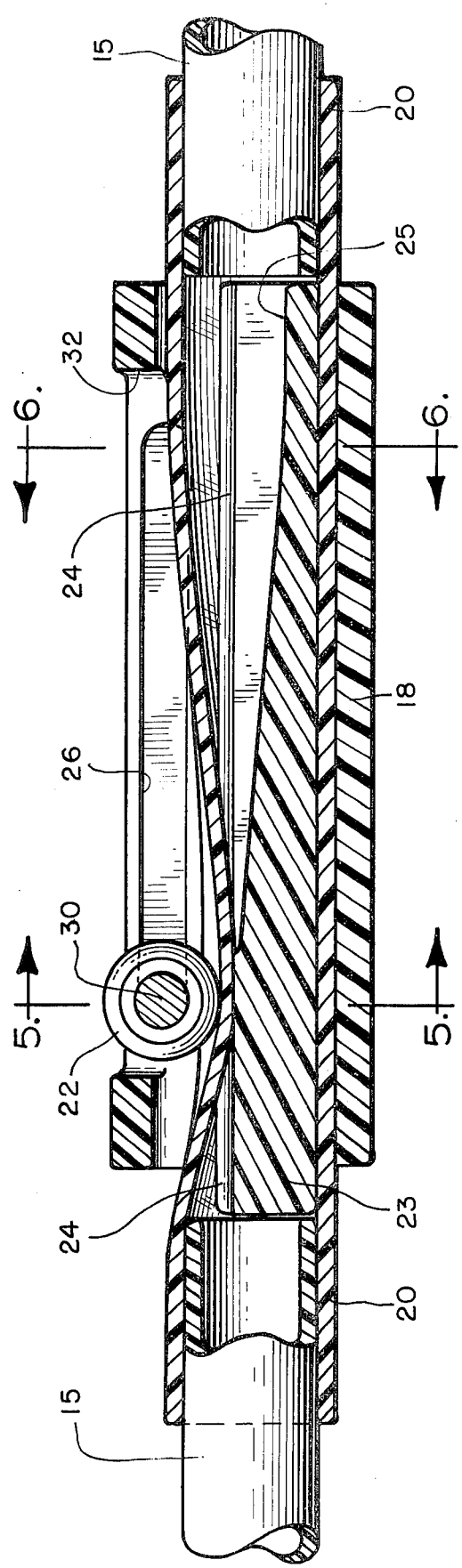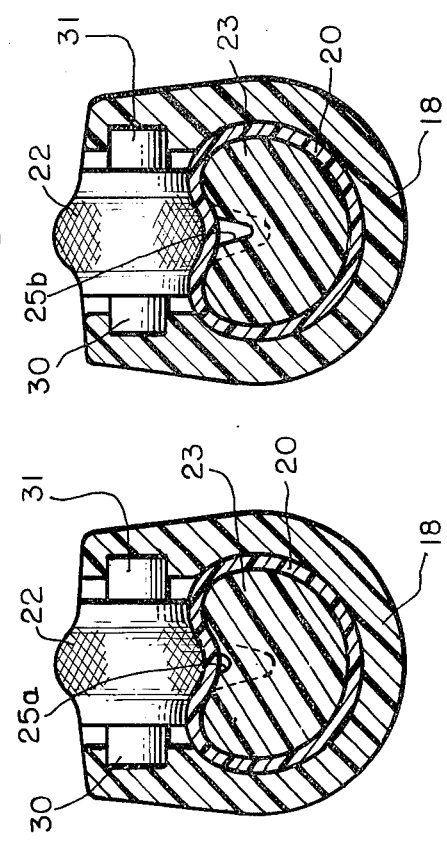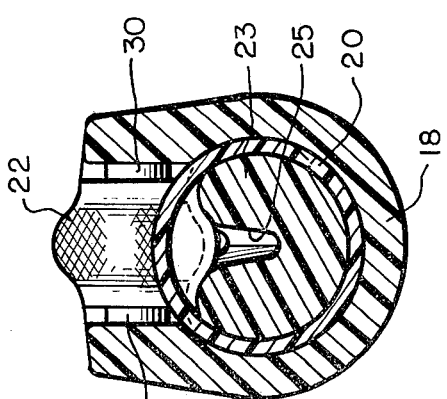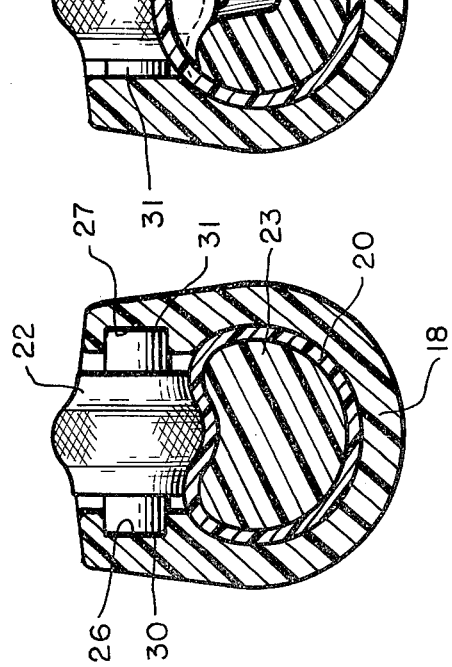

FLOW CONTROL DEVICE

BACKGROUND OF THE INVENTION

The present invention is directed generally to flow control devices, and more particularly to a precision flow control device for use in conjunction with intravenous administration sets or the like wherein accurate control of a low fluid flow rate is required.

Intravenous administration sets, which are widely used in the medical field for injecting blood, nutrient and saline solutions, and other fluids into the human body, normally require an adjustable flow control device for accurately controlling the gravity flow of a fluid being administered from a container suspended above the patent. The requirements imposed on such flow control devices are stringent, since the flow rates through the system are small, typically ranging from 400 ml to 1 ml per hour under a head of approximately 75 cm, and the required accuracy of flow control is often high, particularly where the patient is in a critical condition and an under or over dosage of the fluid being administered may be highly detrimental.

Flow control devices heretofore provided in administration sets have utilized various clamp, lever or roller arrangements for partially crimping the flexible tubing universally used in such sets to restrict the cross-sectional area of the passageway, or lumen, of the tubing. One of the more successful of such compression-type devices consists of a ribbed roller movable along a channel-like housing through which the flexible tubing of the system passes, the opposing wall of the housing being inclined at an angle to the path of the roller so that by varying the position of the roller along the channel the degree of flattening of the tubing, and hence the flow rate through the system, can be controlled. This device is described in U.S. Pat. No. 3,099,429 to C. R. Broman, which is assigned to the present assignee.

One disadvantage of flow control devices of this type is that the flexible tubing of the administration set becomes flattened or otherwise dimensionally deformed as a result of the compression force exerted by the clamp, lever or roller. This deformation may progress with time, with the result that the flow rate in the system changes from the rate initially set, requiring the user to periodically readjust the flow control device if a desired flow rate is to be maintained.

One attempt at overcoming this problem is described in U.S. Pat. No. 3,779,507 to E. W. Clarke. Here it is proposed that a segment of the tubing of the administration set be flattened over a needle-like core of progressively increasing diameter to form a tapering flow-bypass passageway between opposing inside surfaces of the flattened tubing segment. The flattened tubing walls are clamped together to restrict fluid flow to an underlying portion of the tapered passageway, and by moving the clamp along the passageway the cross-sectional area of the operative portion of the flow bypass passage, and hence the flow rate through the system, is controlled. This arrangement has the disadvantage of requiring a high-precision molding operation during manufacture of the administration set for forming the flattened tubing section and the internal bypass passage. During the molding operation the needle-shaped core must be positioned within the tubing with great accuracy, the effectiveness of the flow control being dependent on the accuracy with which the bypass passage is formed in the opposing wall surfaces. Furthermore, in use the flow rate through the administration set nevertheless remains dependent on the cross-sectional area of a passage formed by the same material as the flexible tubing of the administration set, thus not completely avoiding the possibility of changes in cross-sectional area and system flow rate with time.

Accordingly, the present invention is directed to a new and improved flow control device for an administration set or the like which provides more stable flow control.

SUMMARY OF THE INVENTION

The invention is directed to a flow control device for establishing a desired flow rate in a fluid flow system. The device includes a conduit having a resilient wall, and a generally cylindrical insert member disposed within the conduit. The insert member includes an axially-extending depression of uniform cross-section and a flow bypass channel of progressively increasing cross-sectional area along the axis of the depression. Flow control means are included for forcing the wall of the conduit into the depression at a desired location along the axis to restrict flow thereat to a predetermined underlying portion of the flow bypass channel, thus providing the desired flow rate.

BRIEF DESCRIPTION OF THE DRAWINGS

The features of the present invention which are believed to be novel are set forth with particularity in the appended claims. The invention, together with the further objects and advantages thereof, may best be understood by reference to the following description taken in conjunction with the accompanying drawings, in the several figures of which like reference numerals identify like elements, and in which:

FIG. 1 is a perspective view of an administration set incorporating a flow control device constructed in accordance with the invention.

FIG. 2 is an enlarged perspective view of the flow control device of the invention.

FIG. 3 is an enlarged perspective view of the injection-molded insert member utilized in the flow control device.

FIG. 4 is an enlarged cross-sectional view of the flow control device taken along lines 4—4 of FIG. 2.

FIG. 5 is a cross-sectional view of the flow control device taken along lines 5—5 of FIG. 4.

FIG. 6 is a cross-sectional view of the flow control device taken along lines 6—6 of FIG. 4.

FIG. 7 is a cross-sectional view of the flow control device conditioned to obtain a first predetermined flow rate.

FIG. 8 is a cross-sectional view of the flow control device conditioned to obtain a second predetermined flow rate.

DESCRIPTION OF THE PREFERRED EMBODIMENT

Referring to the Figures, and particularly to FIG. 1, a flow control device 10 constructed in accordance with the invention is shown in conjunction with an intravenous fluid administration set 11, which may except for the flow control device be conventional in design and construction. Although the device finds application in other types of fluid flow systems, such as those utilized in chemical laboratories, the device is particularly well suited for controlling the low flow rates of intravenous administration sets and therefore is being shown in such a system.

Basically, the fluid administration set 11 comprises a disposable flow system for conveying a fluid to be intravenously administered from a container 12 to a needle adaptor 13, to which various types of hypodermic needles may be fitted. In use, the container is positioned at a location above the point of fluid injection and gravity flow is relied upon to establish fluid flow through the system.

To control the fluid flow rate the administration set includes as its operative elements a drip chamber 14 and the flow control device 10 of the invention, these elements being connected by appropriate lengths of a small-diameter tubing 15. The drip chamber consists of a partially filled chamber in which drops falling from a drop-forming tubing can be observed, the frequency of the drops being an indication to the user of flow rate in the system. The flow control device, which is shown in detail in the remaining FIGS. 2–7, functions to restrict flow through the system to a rate less than that which would occur by reason of gravity. In practice the flow control device is set by the user by observing the drip rate in drip chamber 14 while simultaneously adjusting the flow control device.

Referring to FIGS. 2–4, the flow control device 10 comprises a conduit 20 formed of polyvinyl chloride or similar material having a high degree of resiliency. Conduit 20 passes through a trough-like housing 21 having side walls 16 and 17 integrally formed with a bottom wall 18 (FIG. 3). Within the housing a roller 22 is constrained for reciprocation along a path parallel to the conduit so as to exert a constant compression force on the conduit and the opposing wall 18 of the housing.

Referring to FIG. 3, an insert member 23, which is preferably formed of a polypropylene resinous plastic material by conventional injection molding techniques, is positioned within the lumen of conduit 20 at a location within the range of movement of roller 22. In accordance with the invention, the upper (as viewed in FIG. 3) side of insert 23 includes a longitudinally-extending valley or depression 24 extending along its entire length. A V-shaped channel 25 of progressively-increasing cross-sectional area extends along the center of depression 24 to provide a fluid bypass passageway. Insert member 23 is positioned in conduit 20 with depression 24 facing the open end of housing 21, as shown in FIG. 2.

A fluid-sealed connection between the conduit and the connecting tubing segments 15 of the administration set is obtained by dimensioning the inside diameter of conduit 20 to closely correspond to the outside diameter of the connecting tubing segments, and bonding the ends of the tubing segments into the ends of the conduit by means of a suitable bonding agent. This arrangement also serves to hold insert member 23 in position within the flow control device 10, since the ends of tubing segments 15 and 16 abut this element.

Fluid flow through device 10 is controlled by roller 22 depressing the wall of conduit 20 into recess 24 on insert member 14, thus restricting flow at that location to the bypass channel 25. Since the cross-sectional area of the channel varies along the axis of the insert member, the location at which the roller compresses the conduit determines the flow rate through the system.

To bring the inside surface of the wall of conduit 20 into a tight liquid-sealed engagement with insert member 23 depression 24 is formed with a gentle compound curvature such that the cross-sectional circumference of the insert member at all points along the axis of the flow control device corresponds very closely to the inside circumference of the conduit wall. This is shown in FIGS. 4–7, which illustrate the uniform non-distorting compression of the conduit wall obtained at various flow settings.

To assist in obtaining a non-distorting compression engagement between the inside wall of the conduit and depression 24 pressure roller 22 is preferably provided with a circumferential surface having a cross-sectional curvature closely corresponding to that of at least the central portion of the compound-curved depression 24 in insert member 23. In this way, the compression of the conduit wall is uniform across its entire cross-section thus facilitating establishment of a liquid seal between conduit 20 and depression 25. Roller 22 is constrained to movement along a path parallel to the axis of conduit 20 and insert member 23 by means of channels 26 and 27 provided in opposing inside surfaces of the inside walls 16 and 17 of housing 21. Roller 22 includes a pair of axially-projecting trunions 30 and 31 which extend into respective ones of channels 26 and 27, the channels being spaced from the conduit so as to bring the roller into constant compression with the wall of conduit 20. An access slot 32 in the top wall of housing 21 allows the user to thumb-position roller 22 at any point along its operating path. Roller 22 may be provided with a surface having knurls or ridges to assist the user in such positioning.

When the wall of the conduit 20 is brought into close liquid-tight engagement with the compound-curved depression 24 in the surface of insert member 23 flow is determined by the cross-sectional area of the flow bypass channel 25 at that point. In FIG. 4 channel 25 has no cross-sectional area and flow is completely cut-off. In FIGS. 6 and 7 the roller is positioned to provide progressively greater bypass areas, and progressively greater flow rates occur. At those locations where roller 22 is not compressing the conduit, such as the location shown in FIG. 5, the wall of conduit 20 returns to its non-compressed state allowing an unrestricted flow to take place through the area 33 which exists between the surface 24 of insert 23 and the inside surface of conduit 20.

In operation, the pressure roller 22 is positioned to cause the wall of conduit 20 to bear against surface 24 at a location where channel 25 has sufficient cross-sectional area to obtain the desired flow rate. In FIG. 6, roller 22 has been positioned at a first intermediate location providing a bypass channel 25a through which a first predetermined flow rate occurs. In FIG. 7, roller 22 has been positioned at a second intermediate location farther to the right (as viewed in FIG. 3) providing a bypass channel 25b of greater cross-sectional area through which a second and greater predetermined flow rate occurs. To obtain a maximum flow rate roller 22 is positioned to the extreme right (as viewed in FIG. 3) of its operating path so that the maximum cross-sectional area of flow bypass channel 25 is available.

When roller 22 is positioned at intermediate locations along conduit 20 the wall of the conduit restores itself to its original condition at locations away from the pressure roller, as shown in FIG. 5. This results in comparatively no flow restriction at these locations, so that the available cross-sectional area of the flow bypass channel 25 is the limiting factor for flow rate in the system.

While the flow control device has been shown with permanently bonded connections to the connecting tubing segments 15 it will be appreciated that other connecting arrangements are possible for the device. For example, conventional luer-type fittings could be provided at either or both ends of the device. Alternatively, various disconnectable arrangements could be utilized where the flow control device is not being utilized in a one-use application and is to be retained for future use.

Rather than fabricate the flow control device as a completely separate unit for attachment to the tubing segments of an administration set, it is also feasible to place insert 23 into a single length of tubing 15. Insert 23 is then positioned at a point along the length of the tubing where the roller clamp is to be applied.

Thus, a novel flow control device has been described which provides positive and stable control of system flow rates, and is therefore particularly well suited for use in intravenous administration sets. Since the flow control device requires a minimal number of components and only simplified assembly techniques, the device is compatible with the high volume production requirements of such administration sets.

It is contemplated that the depression 24 provided on insert member 23 may assume other shapes while still retaining the non-deforming characteristics realized by the invention. Also, the V-shaped flow bypass channel 25 may assume other shapes, such as a rectangular cross-section, while still functioning in accordance with the invention. It is further contemplated that the valve assembly may be manufactured in various sizes with various sizes and shapes of flow control rollers 22 and housings 21 to accommodate the flow requirements of various types of systems.

While a particular embodiment of the invention has been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

I claim:

1. A flow control device for establishing a desired flow rate in a fluid flow system comprising, in combination:
   a conduit having a resilient wall;
   a generally cylindrical insert member disposed within said conduit, said insert member including an axially-extending depression of uniform cross-section;
   a flow bypass channel of progressively increasing cross-sectional area along the axis of said depression, said depression and channel defining in conjunction with said resilient wall a fluid passage through said conduit communicating with the ends of said conduit; and
   flow control means for forcing the wall of said conduit into said depression at a desired location along said axis to restrict flow in said fluid passage to a predetermined underlying portion of said flow bypass channel thereby providing said desired flow rate.

2. A flow control device as defined in claim 1 wherein the circumference of said insert member is substantially equal to the inside circumference of said conduit.

3. A flow control device as defined in claim 1 wherein said depression in cross-section comprises a compound curve.

4. A flow control device as defined in claim 3 wherein the circumference of said insert member is substantially equal to the inside of said conduit.

5. A flow control device as defined in claim 4 wherein said flow control means comprise a roller constrained to movement in a direction parallel to said axis and having a surface engaged to said resilient wall which closely corresponds in cross-section to at least a substantial portion of the surface of said depression.

6. A flow control device as defined in claim 1 wherein said flow control means comprise a roller constrained to movement in a direction parallel to said axis.

7. A flow control device as defined in claim 6 wherein the surface of said roller engaged to said resilient wall closely corresponds in cross-section to at least a substantial portion of said depression.

8. A flow control device as defined in claim 1 wherein said flow bypass channel is V-shaped in cross-section.

9. A flow control device for obtaining a desired flow rate in a fluid flow system comprising, in combination:
   a conduit having a resilient wall of predetermined inside circumference;
   a generally cylindrical insert member disposed within said conduit, said insert member including an axially-extending depression of uniform cross-section, and having a cross-sectional circumference substantially equal to said predetermined inside circumference;
   a flow bypass channel of progressively increasing cross-sectional area along the axis of said depression, said depression and channel defining in conjunction with said resilient wall a fluid passage through said conduit communicating with the ends of said conduit; and
   flow control means including a roller constrained to movement in a direction parallel to said axis for forcing said resilient wall into said depression at a predetermined location along said axis to restrict flow in said fluid passage to a predetermined underlying portion of said flow bypass channel thereby providing said desired flow rate.

10. A flow control device as defined in claim 9 wherein said depression comprises a compound-curved surface.

11. A flow control device as defined in claim 9 wherein the surface of said roller engaged to said resilient wall closely corresponds in cross-section to at least a substantial portion of said depression.

12. A flow control device as defined in claim 9 wherein said flow bypass channel is V-shaped in cross-section.

* * * * *